United States Patent [19]

Lundberg

[11] Patent Number: 5,419,918
[45] Date of Patent: May 30, 1995

[54] METHOD FOR THE MANUFACTURE OF A CONTROLLED RELEASE SOLID UNIT DOSAGE FORM

[75] Inventor: Per Johan G. Lundberg, Mölndal, Sweden

[73] Assignee: Aktiebolaget Astra, Sodertalje, Sweden

[21] Appl. No.: 166,167

[22] Filed: Dec. 10, 1993

Related U.S. Application Data

[63] Continuation of Ser. No. 803,474, Dec. 4, 1991, abandoned.

[30] Foreign Application Priority Data

Dec. 7, 1990 [SE] Sweden ................................ 9003904

[51] Int. Cl.⁶ ................................................ A61K 9/16
[52] U.S. Cl. ...................................... 424/490; 424/489; 424/480; 424/494; 424/484
[58] Field of Search ............... 424/490, 489, 468, 473, 424/464

[56] References Cited

U.S. PATENT DOCUMENTS

| | | | |
|---|---|---|---|
| 4,369,172 | 1/1983 | Schor | 424/468 |
| 4,478,819 | 10/1984 | Hercelin et al. | 424/37 |
| 4,559,384 | 12/1985 | Normura et al. | 524/612 |
| 4,795,327 | 1/1989 | Gaylord et al. | 424/468 |
| 4,871,548 | 10/1989 | Edgren | 424/464 |
| 4,971,805 | 11/1990 | Kitanishi et al. | 424/494 |
| 5,024,842 | 6/1991 | Edgren | 424/473 |
| 5,071,646 | 12/1991 | Malkowska et al. | 424/497 |

FOREIGN PATENT DOCUMENTS 0157695 9/1985 European Pat. Off. .

OTHER PUBLICATIONS

Dow 1987, "Formulating Release with Methocel cellulose ethers", ppp. 1–32.

*Primary Examiner*—Thurman K. Page
*Assistant Examiner*—William E. Benston, Jr.
*Attorney, Agent, or Firm*—White & Case

[57] ABSTRACT

A method for the manufacture of oral controlled release dosage units containing hydroxypropyl methylcellulose wherein the aqueous granulation is performed in the presence of one or more solutes, which inhibit gel formation during the granulation but allows the formation of a gel when administered orally. Also the new dosage units prepared according to the invention are included.

11 Claims, No Drawings

METHOD FOR THE MANUFACTURE OF A CONTROLLED RELEASE SOLID UNIT DOSAGE FORM

This application is a continuation of application Ser. No. 07/803,474, filed Dec. 4, 1991, and now abandoned.

BACKGROUND OF THE INVENTION

1. Field of the Invention

This invention relates to a method of manufacture of a controlled release solid unit dosage form based on the hydrophilic gel matrix principle for administration of medicaments. Also the solid unit dosage forms are included. Specifically, this invention relates to the use of a waterbased granulating solution containing an additive which inhibits gel formation of hydroxypropyl methylcellulose (HPMC) during granulation but not of the gelling of the final dosage form in vivo, which is necessary for its function.

2. Background and Prior Art

Granulation of hydrophilic gel matrix dosage forms containing HPMC as main gelling agent, has usually been performed with ethanol and methanol (U.S. Pat. No. 4,871,548), isopropanol and aqueous mixtures thereof (EP-A-157695). According to the product information brochure from a manufacturer of this polymer, (DOW 1987, 'Formulating for controlled release with METHOCEL cellulose ethers', page 24-5) aqueous granulation of very finely sized particles can be applied, but it is also pointed out that in doing so, a situation may occur, where the granules obtained are very hard and difficult to grind. This is connected with a high polymer content of the granulate. The proposed way in the brochure to minimize these problems is to granulate with a hydroalcoholic solution and thereby reduce the water content in the system.

Production of such dosage forms has also been performed by water granulation of parts of the composition, exluding the gelling agent. This is described in the above cited EP-A-157695. In other cases direct compression have been used (U.S. Pat No. 4,369,172).

SUMMARY OF THE INVENTION

The object of the present invention is to provide a method of manufacture, which includes a water-based granulation process for controlled release dosage forms containing HPMC as gel forming agent.

The method provides homogenous granulates with desired flow properties and enables production of controlled release tablets without the use of volatile organic solvents.

It has been found that this waterbased granulation procedure for HPMC based dosage forms can be successfully performed by the use of a granulating solution containing an additive of a polyhydric alcohol or other substances which inhibit the rapid hydration of the gelling substance or substances during granulation.

DETAILED DESCRIPTION OF THE INVENTION

According to the present invention, advantages and improvements over prior art describing water-based granulation of HPMC based dosage forms can be obtained by adding one or more substances, dissolved in the granulating solution. The solutes inhibit the rapid hydration of HPMC during the said process step. Examples of such substances are polyhydric alcohols or other substances defined below. Without the addition of the above-mentioned substances very hard or flaky granules with poor flowability are produced.

The polyhydric alcohols, effective in the water-based granulation of this invention, include, but are not limited to, polyethylene glycols (PEG), polypropylene glycols (PPG), poloxyethylene-polyoxypropylene glycols (Pluronics ®) sugar alcohols such as sorbitol, mannitol, xylitol etc and sugars, for instance such as sucrose, galactose, glucose, fructose. Another substance found to achieve the same effect is polyvinyl pyrrolidone (PVP). The said additive substances, usually in the concentration range between 20–50% w/w, preferably between 25–45%, have been found to be effective on, but are not limited to, viscosity grades of hydroxypropyl methylcelluloses including 50 cps and high viscosity grades of 4,000, 10,000 and 15,000 cps.

In the following examples the term "active substance" is any compound suitable as the active component in a pharmaceutical dosage form.

EXAMPLES

Example 1

Controlled release tablets were prepared by granulating 19.0 parts active substance, 100 parts lactose, 78.0 parts HPMC 50 cps, 60 parts HPMC 10,000 cps, 25 parts hydroxypropyl cellulose (HPC), with a solution of 30 parts PEG 6,000 dissolved in 70 parts of water. The dried granulate was lubricated with 3.2 parts sodium stearyl fumarate.

As reference preparation (Ref.ex. I) the same ingredients were granulated with pure water, that is without the addition of the polyhydric alcohol.

| Ingredient | Example 1 mg/tablet | Ref. ex. I mg/tablet |
| --- | --- | --- |
| 1. Active substance | 19.0 | 19.0 |
| 2. Lactose pwd | 100.0 | 100.0 |
| 3. HPMC (Metolose ® 60SH50) | 78.0 | 78.0 |
| 4. HPMC (Methocel ® E10MCR) | 60.0 | 60.0 |
| 5. HPC (Klucel ® LF) | 25.0 | 25.0 |
| 6. PEG (Carbowax ® 6000) | 35 | — |
| 7. Water, purified | 81.7 | 117 |
| 8. Sodium stearyl fumarate (Pruv ®) | 3.2 | 3.2 |

Ingredients 1 to 5 were mixed. The mixture was granulated with a solution made of ingedients 6 and 7. After drying, the granulate was mixed with the lubricant, 8. The granulate obtained in ref.ex. I, was hard and flaky, and the milling was almost impossible to perform. Some of it had to be ground with pestle and mortar. No difficulties were experienced with the granulate in example 1.

Compression to tablets were performed on a Korsch Pharmapress 100 with 10 mm circular punches. The tablet machine was equipped with compression force registration.

| | Ex. 1 | Ref. ex. I |
| --- | --- | --- |
| Tablet weight: | 320 mg | 319 mg |
| Tablet compression force (kN): | 13.20 | 11.2 |
| Tablet hardness (kP): | 5.5 | 5.6 |

Example 2.

Controlled release tablets were prepared by granulating 95.0 parts active substance, 40.0 parts HPMC 50 cps, 160 parts HPMC 10,000 cps, 50 parts HPC with a solution of 30 parts PEG 6,000 dissolved in 70 parts of water. The dried granulate was lubricated with 3.6 parts of sodium stearyl fumarate.

As a reference preparation (Ref.ex. II) the ingredients were granulated with 99.5% ethanol and then lubricated in the same manner.

| Ingredient | Example 2 mg/tablet | Ref. ex. II mg/tablet |
| --- | --- | --- |
| 1. Active substance | 95.0 | 95.0 |
| 2. HPMC (Metolose ® 60SH50) | 40.0 | 40.0 |
| 3. HPMC (Methocel ® E10MCR) | 160.0 | 160.0 |
| 4. HPC (Klucel ® LF) | 50.0 | 50.0 |
| 5. PEG (Carbowax ® 6000) | 30 | — |
| 6. Water, purified | 70 | — |
| Ethanol 99.5% | — | 261 |
| 7. Sodium stearyl fumarate (Pruv ®) | 3.6 | 3.3 |

Ingredients 1 to 4 were mixed. The mixture was granulated with a solution made of ingredients 5 and 6. After drying the granulate was mixed with the lubricant, 7.

Compression to tablets were performed on a Korsch Pharmapress 100 with 11 mm circular punches. The tablet machine was equipped with compression force registration.

| | Example 2. | Ref. ex. II |
| --- | --- | --- |
| Tablet weight: | 379 mg | 348 mg |
| Tablet compression force (kN): | 14.0 | 8.6 |
| Tablet hardness (kP): | 5.3 | 5.5 |

The release rate was determined from 6 individual tablets in USP dissolution apparatus 2 with the paddle rotating at
100 r/min and the tablet placed in a stationary basket above the paddle. 500 ml buffer solution pH 6.8 kept at 37° C. was used as dissolution medium.

| hours | Ex. 2 cumulative % released average (min-max) | Ref. ex. II cumulative % released average (min-max) |
| --- | --- | --- |
| 2 | 14 (14–15) | 15 (14–15) |
| 4 | 25 (24–25) | 24 (23–25) |
| 6 | 36 (35–37) | 34 (33–35) |
| 10 | 52 (51–54) | 51 (48–52) |
| 24 | 98 (96–101) | 91 (87–93) |

In vitro data obtained show no difference in the release rates of the two formulations.

Examples 3–4

Controlled release tablets were prepared by granulating 38.0 parts active substance, 19.5 parts lactose, 37.2 parts HPMC 50 cps, 82.8 parts HPMC 10,000 cps, 37.5 parts HPC with a solution of 30 parts PEG 6,000 (Ex. 3) or PVP K-25 (Ex. 4) dissolved in 70 parts of water. The dried granulate was lubricated with 1.2 parts of sodium stearyl fumarate.

| Ingredient | Example 3 mg/tablet | Example 4 mg/tablet |
| --- | --- | --- |
| 1. Active substance | 38 | 38 |
| 2. Lactose pwd | 19.5 | 19.5 |
| 3. HPMC (Metolose ® 60SH50) | 37.2 | 37.2 |
| 4. HPMC (Methocel ® E10MCR) | 82.8 | 82.8 |
| 5. HPC (Klucel ® LF) | 37.5 | 37.5 |
| 6. PEG (Carbowax ® 6000) | 30 | — |
| PVP (Povidone ® K-25) | — | 30 |
| 7. Water, purified | 70 | 70 |
| 8. Sodium stearyl fumarate (Pruv ®) | 1.2 | 1.2 |

Ingredients 1 to 5 were mixed. The mixture was granulated with a solution made of 6 and 7. After drying the granulate was mixed with 8.

Compression to tablets were performed on a Korsch Pharmapress 100 with 9 mm circular punches. The tablet machine was equipped with compression force registration.

| | Example 3 | Example 4 |
| --- | --- | --- |
| Tablet weight: | 246 mg | 246 mg |
| compression force (kN): | 10.4 | 10.9 |
| tablett hardness (kP): | 4.9 | 7.0 |

The release rate was determined in USP dissolution apparatus 2 with the paddle rotating at 100 r/min and the tablet placed in a stationary basket above the paddle. 500 ml buffer solution pH 6.8 kept at 37° C. was used as dissolution medium.

| | Cumulative % released Average (min-max) | |
| --- | --- | --- |
| | Example 3. | Example 4. |
| 2 h | 24 (23–24) | 23 (23–24) |
| 4 h | 40 (38–43) | 40 (29–41) |
| 6 h | 56 (54–60) | 57 (55–58) |
| 10 h | 85 (81–91) | 85 (82–87) |

The examples show that PEG 6000 and PVP K-25 both function in the process.

Examples 5–8

Controlled release tablets were prepared by granulating 38.0 parts active substance, 19.5 parts lactose, 51.4 parts HPMC 50 cps, 68.6 parts HPMC 10,000 cps, 37.5 parts HPC with a solution of 30 parts substances according to the table below, dissolved in 70 parts of water. The dried granulate was lubricated with 2.5 parts of sodium stearyl 30 fumarate.

| | Example | | | |
| --- | --- | --- | --- | --- |
| | 5 | 6 | 7 | 8 |
| Ingredient | mg/tablet | | | |
| 1. Active substance | 38 | 38 | 38 | 38 |
| 2. Lactose pwd | 19.5 | 19.5 | 19.5 | 19.5 |
| 3. HPMC (Metolose ® 60SH50) | 51.4 | 51.4 | 51.4 | 51.4 |
| 4. HPMC (Methocel ® E10MCR) | 68.6 | 68.6 | 68.6 | 68.6 |
| 5. HPC (Klucel ® LF) | 37.5 | 37.5 | 37.5 | 37.5 |
| 6. PEG (Carbowax ® 6000) | 30 | — | — | — |
| PEG (Carbowax ® 20M) | — | 30 | — | 20 |
| PEG (Polyox ® WSRN 10) | — | — | — | 10 |
| Sorbitol | — | — | 30 | — |
| 7. Water, purified | 70 | 70 | 70 | 70 |
| 8. Sodium stearyl fumarate (Pruv ®) | 2.5 | 2.5 | 2.5 | 2.5 |

Ingredients 1 to 5 were mixed. The mixture was granulated with a solution made of 6 and 7. After drying the granulate was mixed with 8.

Compression to tablets was performed on a Korsch Pharmapress 100 with 9 mm circular punches. The tablet machine was equipped with compression force registration.

|  | Ex. 5 | Ex. 6 | Ex. 7 | Ex. 8 |
| --- | --- | --- | --- | --- |
| Tablet weight (mg): | 247 | 247 | 247 | 247 |
| compression force (kN): | 11.9 | 10.6 | 10.9 | 11.0 |
| tablet hardness (kP): | 5.1 | 6.1 | 8.7 | 5.5 |

The release rates were determined in USP dissolution apparatus 2 with the paddle rotating at 100 r/min and the tablet placed in a stationary basket above the paddle. 500 ml buffer solution pH 6.8, kept at 37° C., was used as dissolution medium.

| | Cumulative % released Average (min-max) | | | |
| --- | --- | --- | --- | --- |
|  | Ex. 5 | Ex. 6 | Ex. 7 | Ex. 8 |
| 2 h | 26 (25–27) | 24 (23–25) | 25 (24–26) | 26 (24–27) |
| 4 h | 46 (44–46) | 43 (41–44) | 45 (43–46) | 44 (42–46) |
| 6 h | 64 (63–66) | 62 (60–64) | 64 (62–67) | 62 (59–64) |
| 10 h | 99 (96–108) | 99 (97–102) | 96 (93–99) | 98 (91–103) |

Examples 9–10

Controlled release tablets were prepared by granulating 54.3 parts active substance, 30.0 parts mannitol, 154 parts HPMC 50 cps, 221 parts HPMC 10,000 cps, 37.5 parts HPC, 0.3 parts propyl gallate with a solution of 45 parts PEG 20,000 (Ex. 9) or PVP K-25 (Ex. 10) dissolved in 105 parts of water. The dried granulate was lubricated with 2.7 parts of sodium stearyl fumarate.

| Ingredient | Example 9 mg/tablet | Example 10 |
| --- | --- | --- |
| 1. Active substance | 54.3 | 54.3 |
| 2. Mannitol pwd | 30.0 | 30.0 |
| 3. HPMC (Metolose ® 60SH50) | 154.0 | 154.0 |
| 4. HPMC (Methocel ® E10MCR) | 221.0 | 221.0 |
| 5. HPC (Klucel ® LF) | 37.5 | 37.5 |
| 6. Propyl gallate | 0.3 | 0.3 |
| 7. PEG (Carbowax ® 20M) | 45.0 | — |
|    PVP (Povidone ® K-25) | — | 45.0 |
| 8. Water | 105.0 | 105.0 |
| 9. Sodium stearyl fumarate (Pruv ®) | 2.7 | 2.7 |

Ingredients 1 to 6 were mixed. The mixture was granulated with a solution made of 7 and 8. After drying the granulate was mixed with 9.

Compression to tablets were performed on a Korsch Pharmapress 100 with 11 mm circular punches. The tablet machine was equipped with compression force registration.

|  | Example 9 | Example 10 |
| --- | --- | --- |
| Tablet weight: | 545 mg | 545 mg |
| compression force (kN): | 20 | 19 |
| tablet hardness (kP): | 7.7 | 12.2 |

The release rate was determined in USP dissolution apparatus 2 with the paddle rotating at 100 r/min and the tablet placed in a stationary basket above the paddle. 500 ml buffer solution pH 6.8 kept at 37° C. was used as dissolution medium.

| | Cumulative % released Average (min-max) | |
| --- | --- | --- |
|  | Example 9 | Example 10 |
| 2 h | 17 (17–18) | 18 (17–18) |
| 4 h | 28 (28–29) | 28 (28–29) |
| 6 h | 38 (38–39) | 38 (37–39) |
| 10 h | 55 (54–56) | 54 (53–56) |
| 16 h | 74 (73–76) | 73 (71–74) |

The examples show that PEG 20000 and PVP K-25 both function in the process.

The best mode known at present is to prepare dosage forms according to examples 9 or 10.

I claim:

1. A method for the manufacture of an oral controlled release hydrophilic matrix gel forming dosage composition containing an active substance, which comprises the step of granulating a mixture of the active substance and a suitable amount of hydroxypropylmethylcellulose (HPMC) in a water solution of 20% to 50% of one or more solutes as additives suitable for minimizing the rapid hydration and gel formation of HPMC during the water-based based granulation process, but which allows the gel formation of HPMC in a liquid environment when administered orally to mammals.

2. The method according to claim 1 wherein the solution contains 25–45% of the solute.

3. The method according to claim 1 wherein the amount of HPMC in the dosage composition is more than 25% w/w.

4. The method according to claim 1, 2, or 3 wherein the solute is polyethylene glycol with a molecular weight in the range 400–100,00.

5. The method according to claim 1, 2 or 3 wherein the solute is selected from the group consisting of sorbitol, mannitol and xylitol.

6. The method according to claim 1, 2 or 3 wherein the solute is selected from the group consisting of sucrose, glucose and fructose.

7. The method according to claim 1, 2 or 3 wherein the solute is selected from the group consisting of polyxyethylene-polyoxypropylene glycols and polypropylene glycol.

8. The method according to claim 1, 2 or 3 wherein the solute is polyvinyl pyrrolidone.

9. An oral controlled release dosage from prepared according to claim 1.

10. The method according to claim 1, 2 or 3 wherein the solute is polyhydric alcohol.

11. The method according to claim 1, 2 or 3 wherein the HPMC is of a different viscosity selected from the group consisting of 50 cps, 4,000 cps, 10,000 cps and 15,000 cps.

* * * * *

UNITED STATES PATENT AND TRADEMARK OFFICE
CERTIFICATE OF CORRECTION

PATENT NO. : 5,419,918
DATED : May 30, 1995
INVENTOR(S) : Per Johan G. Lundberg

It is certified that error appears in the above-indentified patent and that said Letters Patent is hereby corrected as shown below:

col. 6, line 44, change "100,00" to --100,000--;

col. 6, line 53, change "polyxyethylene" to --polyoxyethylene--;

col. 6, line 54, change "glycol" to --glycols--;

col. 6, line 57, change "from" to --form--;

col. 6, line 60, insert --a-- after "is;"

col. 6, line 62, delete "is of a" and insert --component results from blending HPMCs of--, and change "viscosity" to --viscosities--.

Signed and Sealed this

Seventeenth Day of February, 1998

Attest:

BRUCE LEHMAN

Attesting Officer     Commissioner of Patents and Trademarks